United States Patent [19]

Pearson et al.

[11] Patent Number: 5,459,566
[45] Date of Patent: Oct. 17, 1995

[54] MULTIPLE PASS GAS ABSORPTION CELL UTILIZING A SPHERICAL MIRROR OPPOSITE ONE OR MORE PAIR OF OBLIQUELY DISPOSED FLAT MIRRORS

[75] Inventors: Richard Pearson, Cupertino; Dana H. Lynch, Montara; William D. Gunter, San Jose, all of Calif.

[73] Assignee: The United States of America as represented by the Administrator of the National Aeronautics and Space Administration, Washington, D.C.

[21] Appl. No.: 231,096

[22] Filed: Apr. 22, 1994

[51] Int. Cl.$^6$ ............................................. G01N 1/10
[52] U.S. Cl. .................... 356/246; 356/440; 250/343; 250/575; 250/576
[58] Field of Search ................... 356/432, 437, 356/440, 445, 246; 250/573, 575, 576, 343, 345

[56] References Cited

U.S. PATENT DOCUMENTS

| | | | |
|---|---|---|---|
| 3,726,598 | 4/1973 | Gilby | 356/244 |
| 4,035,963 | 7/1977 | Gilby | 51/324 |
| 4,209,232 | 6/1980 | Chernin | 356/246 |
| 4,322,621 | 3/1982 | Aagard | 356/440 |
| 4,626,078 | 12/1986 | Chernin et al. | |
| 4,676,652 | 6/1987 | Chernin et al. | 356/246 |
| 5,009,493 | 4/1991 | Koch et al. | 356/246 |
| 5,125,742 | 6/1992 | Wilks | 356/246 |

*Primary Examiner*—Richard A. Rosenberger
*Assistant Examiner*—Jason D. Eisenberg
*Attorney, Agent, or Firm*—Kenneth L. Warsh; Guy Miller; John G. Mannix

[57] ABSTRACT

A method and apparatus for passing light bundles through a multiple pass sampling cell. The multiple pass sampling cell includes a sampling chamber having first and second ends positioned along a longitudinal axis of the sampling cell. The sampling cell further includes an entrance opening, located adjacent the first end of the sampling cell at a first azimuthal angular position. The entrance opening permits a light bundle to pass into the sampling cell. The sampling cell also includes an exit opening at a second azimuthal angular position. The light exit permits a light bundle to pass out of the sampling cell after the light bundle has followed a predetermined path.

13 Claims, 3 Drawing Sheets

MULTIPLE PASS GAS ABSORPTION CELL UTILIZING A SPHERICAL MIRROR OPPOSITE ONE OR MORE PAIR OF OBLIQUELY DISPOSED FLAT MIRRORS

ORIGIN OF THE INVENTION

The invention described herein was made by an employee of the United States Government and may be manufactured and used by or for the Government for governmental purposes without payment of any royalties thereon or therefor.

BACKGROUND OF THE INVENTION

1. Field Of The Invention

The invention relates to gas absorption cells and, more particularly, to a compact multiple pass open path gas absorption measurements in a compact space using an extended light source, such as thermal, hot filament, gas discharge, etc.

2. Description of the Related Art

Optical sampling cells are commonly utilized in IR spectrophotometers to measure the concentration of gas within the sampling cells. Specifically, multiple pass optical sampling cells are widely used in IR spectrophotometers to measure low concentration gases or gases having very faint absorption bands. Both single and multiple pass sampling cells have a number of limitations which diminish their effectiveness as analytical tools.

Specifically, single pass sampling cells conventionally have an optical path length which is essentially the same as the physical path length. Single pass sampling cells are designed such that a light bundle enters the cell at one end and exits at the other end without making any reflections. As a result, the cell length required for measuring gas absorption may be impractical when a gas having a low absorption coefficient is measured. Additionally, similar problems arise when low densities or concentrations of gas are present. It should be noted that "light" or "light bundle" as referred to herein means any form of electromagnetic radiation used to measure the absorption of predetermined gases.

When single pass sampling cells are used with extended light sources, the light source may strike the interior walls of the sampling cell at shallow angles and be reflected many times. Clearly, this reflected light does not follow the simple intended path. Instead, multiple reflections cause the reflected light to take a longer path through the sampling cell. When absorbance in a sampling cell is interpreted by applying the Beer-Lambert relation, which assumes a single well-defined length, such reflections can cause significant errors. This effect is often exaggerated for longer sampling cells with narrow diameters.

For applications involving the measurement of reactive trace gases at low pressure, it is important to minimize collisions with the sampling cell walls and to move the gas through the cell rapidly so that the composition of the sample does not change during the measurement. Both conditions are difficult to achieve with a single pass sampling cell small enough for use with practical instruments.

With regard to multiple pass sampling cells, the White cell and the Herriott cell are exemplary of commonly employed sampling cells. The White cell utilizes a cell having a pair of mirrors opposite the end of the cell through which light enters. Each of the mirrors must equal or exceed the size of the light bundle's diameter after it traverses the sampling cell once. It should be noted that the diameter of the light bundle, as referred to in the body of this application, is meant to indicate the diameter of the light bundle taken in a plane perpendicular to the longitudinal axis of the light bundle. Each of the paired mirrors must be larger than the expanded light bundle, so that end of the sampling cell must be more than twice the light bundle diameter in at least one direction.

The Herriott cell includes two spherical mirrors of equal radii on opposite ends of the sampling cell. The centers of the light bundle makes repeated reflections from the mirrors, striking them at locations away from the centers of the mirrors. As a result, the mirrors must have diameters considerably larger than the maximum diameter of the light bundle. Thus, the Herriott cell is best suited for use with small, well disciplined light bundles.

Multiple pass sampling cells provide long optical path length in a relatively small volume. They are, however, very sensitive to misalignment. A small change in mirror separation can change the number of reflections and produce large changes in the path length. In addition, when prior multiple pass cells are employed with an extended source, it is possible for light to follow a path significantly different from the intended path. This introduces inaccuracies into measurements that generally have little room for error.

Additionally, where a sampling cell is used for accurately measuring gas concentration by applying the Beer-Lambert relation, it is necessary to accurately determine the length of the light path within the sampling cell. The problems discussed above can adversely affect the accuracy of measurements, are difficult to quantify, and consequently make it very difficult to apply the principles of the Beer-Lambert relation.

U.S. Pat. No. 4,676,652 to Chernin et al. discloses a multiple pass optical system using curved transfer mirrors in which light strikes one mirror of a pair at a more glancing angle than the other. Other U.S. patents disclosing a variety of optical systems include U.S. Pat. Nos. 3,726,598 to Gilby; 4,035,963 to Gilby; 4,209,232 to Chernin; 4,626,078 to Chernin et al.; 5,009,493 to Koch et al.; and 5,125,742 to Wilks.

A continuing need exists for a multiple pass sampling cell capable of providing convenient, reliable and efficient measurements.

SUMMARY OF THE INVENTION

An object of the present invention is to provide a multiple pass sampling cell which provides convenient, reliable and efficient measurements of low concentration gases and gases having relatively faint absorption bands.

Another object of the invention is to provide a multiple pass sampling cell having ends only slightly larger in diameter than the largest diameter of the light bundle.

A further object of the present invention is to provide a multiple pass sampling cell capable of facilitating the passage of large quantities of light through the sampling cell.

Another object of the present invention is to provide a multiple pass sampling cell having relatively large tolerances for the parts and mechanical assembly of the sampling cell.

A further object of the invention is to provide a sampling cell capable of controlling the path through which a light bundle is directed, so that the light inlet and outlet are spaced apart azimuthally.

These and other object are achieved by providing a multiple pass gas absorption cell which includes a gas chamber having first and second opposite axial ends and a longitudinal axis, a light inlet disposed at the first axial end of the gas chamber, a light outlet disposed at the first axial end and being on a common radius with the light inlet but at a different azimuthal position, first reflective means, fixedly disposed at the second axial end of the gas chamber, for directing light longitudinally through the gas chamber towards the first axial end, and second reflective means, fixedly disposed at the first axial end of the gas chamber, for directing light reflected off the first reflective means in a direction transverse the longitudinal axis of the gas chamber and longitudinally through the gas chamber towards the second axial end.

Other objects, advantages and salient features of the invention will become apparent from the following detailed description, which taken in conjunction with the annexed drawings discloses a preferred, but non-limiting, embodiment of the subject invention.

DETAILED DESCRIPTION OF THE INVENTION

Figure 1:
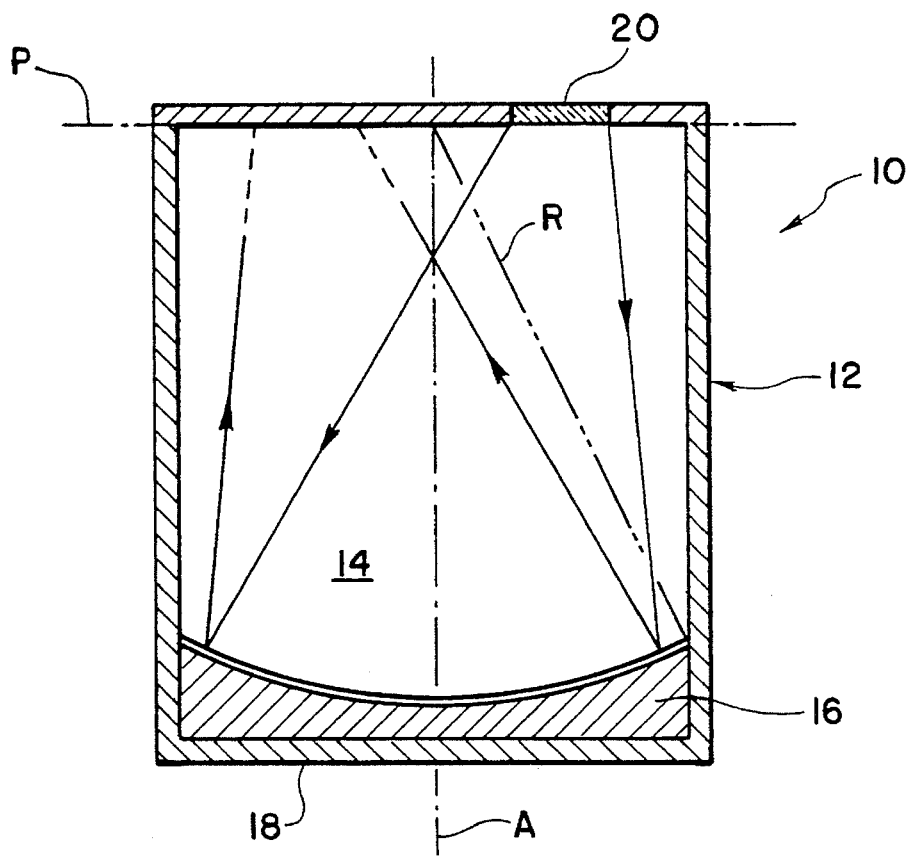
FIG. 1 is a schematic, vertical sectional view of a gas absorption cell of the present invention, taken along line I—I of FIG. 2, without mirror pairs disposed within the gas chamber or a light outlet, for purposes of illustrating principles of operation of the present invention.
Figure 2:
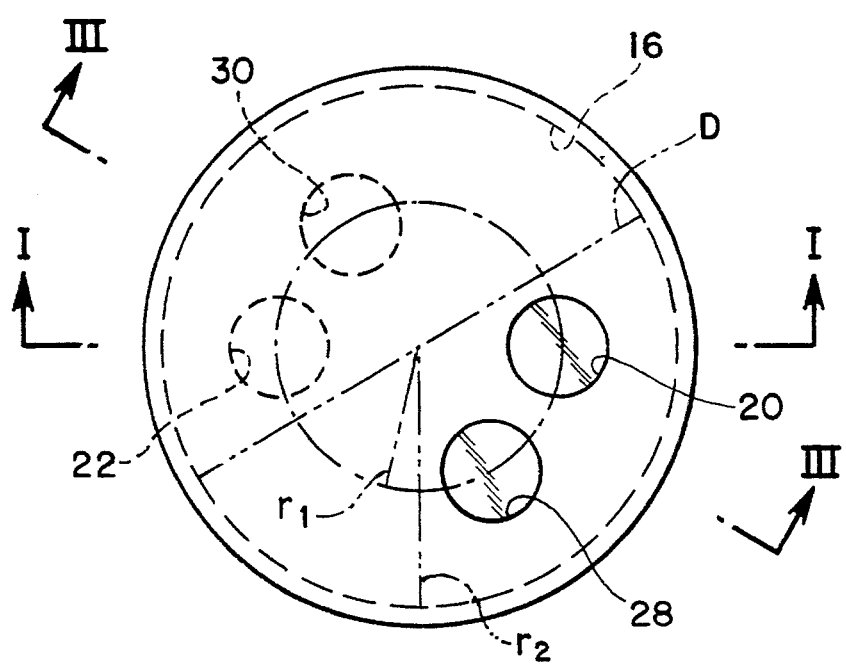
FIG. 2 is a top view of the cell of FIG. 1.

Referring to FIGS. 1 and 2, a gas absorption cell 10 includes a cylindrical body 12 which defines a sealed gas chamber 14 having first and second opposite axial ends and a longitudinal axis "A". Any suitable material can be used to construct the body 12, which can be constructed in shapes other than cylindrical.

A spherical mirror 16 having a concave reflective surface 18 is fixedly positioned at the second end of the chamber 14. The spherical mirror 16 has a diameter "D" only slightly larger than the largest diameter of the incoming light bundle which diverges onto the surface 18. The light bundle is centered on the mirror 16, as shown in FIG. 1.

A light inlet 20, or entrance aperture, is approximately one mirror radius "R" distant from the mirror 16, and is off-axis at a radius "$r_1$" less than the physical radius "$r_2$" of the mirror 16, as seen in FIG. 2.

After being reflected from the mirror 16, the light would, without further mirrors, come to a focus in the plane "P" of the entrance aperture 20, but diametrically opposite it as shown by the broken circle 22. Without further reflecting means, the device shown in FIG. 1 would be a two-pass structure. According to the present invention, reflective means are disposed within the chamber 14 to multiply the number of passes, and simultaneously, change the azimuthal position of the light exit location.

Figure 3:
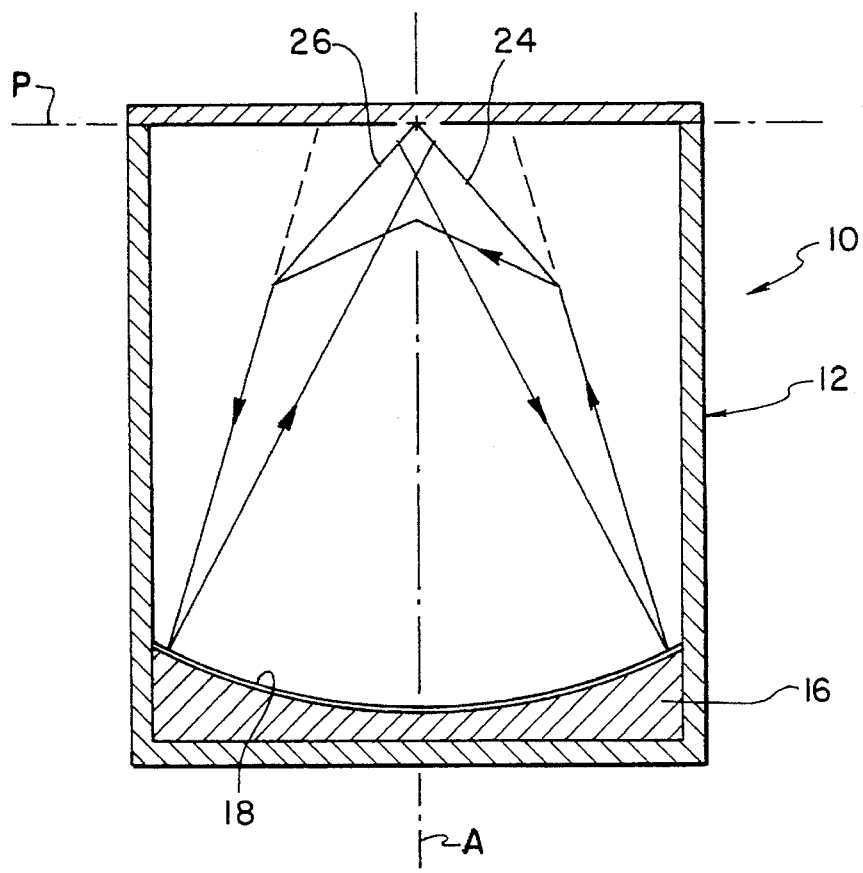
FIG. 3 is a schematic, vertical sectional view of a gas absorption cell of FIG. 1, taken along line III—III of FIG. 2, with a first pair of mirrors disposed in the chamber to generate a four-pass structure.

As seen in FIG. 3, a pair of flat mirrors 24 and 26, obliquely disposed with respect to each other, are mounted in the chamber 14 in an upper portion thereof. Thus, before reaching the focal area 22, the first mirror of the pair reflects the light into a plane perpendicular to the axis A of the chamber 12. Within that plane the axis of the light bundle is also perpendicular to the axis of the cell.

Subsequent to forming an image of the entrance, the light bundle strikes the second mirror of the pair, which reflects the bundle to strike the center of the mirror 16. On reflection from the mirror 16, the light again travels toward a focus in the plane of the entrance 20. The effect of the two oblique mirrors has been to assure that this return beam will not be at the entrance, but at a different azimuthal angle around the cell axis A. If the four passes of light that result yield a sufficiently long optical path, the light may be allowed to exit the cell, as at light exit 28. Broken circle 30, as well as broken circle 22, represent locations where beams reflected from the oblique mirrors would appear on the entrance (and exit) plane if they were extended (forward or backward as necessary) through the mirrors to that plane.

Figure 5:
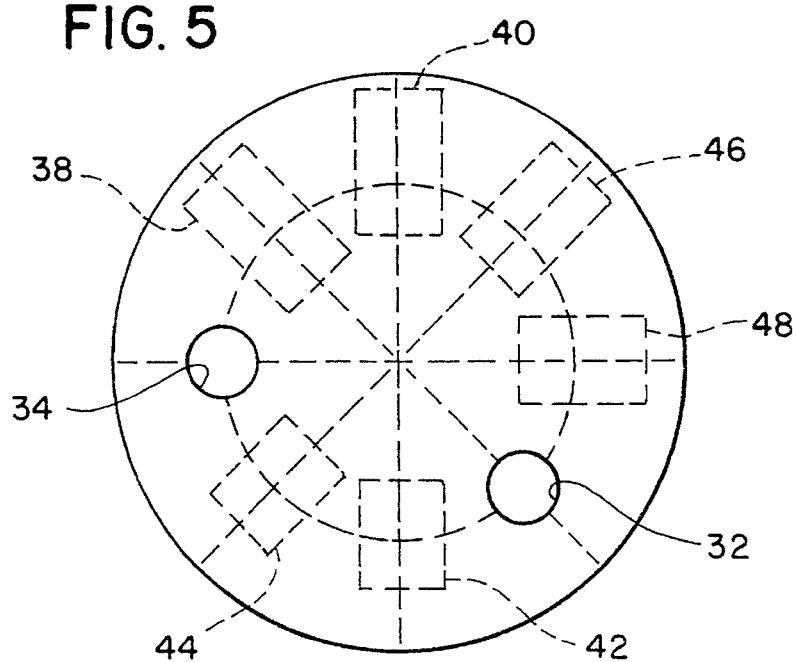
FIG. 5 is a top plan view of the embodiment of FIG. 4, showing the radial locations of the mirror pairs and the light inlet and outlet.
Figure 4:
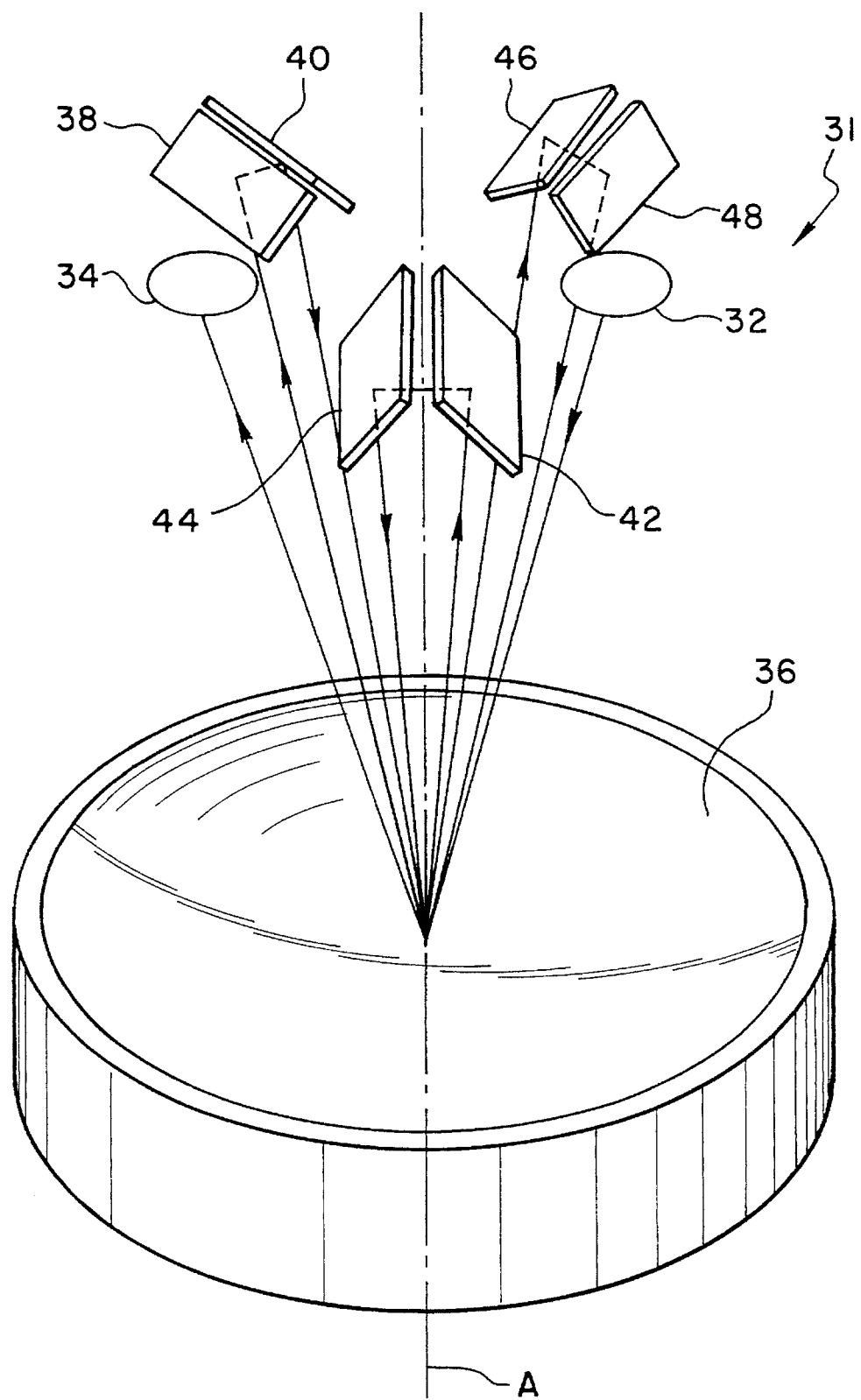
FIG. 4 is a schematic, perspective view of a second embodiment of the present invention, with mirror pairs sufficient to generate eight light passes through the gas chamber.

If more passes are needed one or more additional pairs of oblique mirrors can be added to the illustrated structure to thereby extend the tour of the light through the cell 10. FIGS. 4 and 5 are of an eight-pass cell 30, in which the central rays of light are shown to clarify the number of passes. A body forming the gas chamber has been removed to better illustrate the light path. The inlet 32 and outlet 34 foci are actually located above the mirror pairs, and would be formed in the end plate fitted over the open end of the body which forms the gas chamber.

The central ray of light entering the chamber through inlet 32 strikes the spherical mirror 36 in the center, and is reflected back to the plane of the inlet 32, in the same radius as the inlet 32 but at a diametrically opposite position. At this position a first mirror 38 of a first mirror pair is positioned to direct the ray in a direction perpendicular to the axis A of the chamber. A second mirror 40 of the first mirror pair is positioned adjacent the first mirror 38, and obliquely thereto, to redirect the central ray back to the center of the mirror 36.

A first mirror 42 of a second mirror pair is positioned to redirect the central ray after reflecting off the mirror 36 in a direction perpendicular to the axis A of the chamber. A second mirror 44 of the second mirror pair is positioned adjacent the first mirror 42, and obliquely thereto, to redirect the central ray back to the center of the mirror 36.

A first mirror 46 of a third mirror pair is positioned to redirect the central ray after reflecting off the mirror 36 in a direction perpendicular to the axis A of the chamber. A third mirror 48 of the second mirror pair is positioned adjacent the first mirror 46, and obliquely thereto, to redirect the central ray back to the center of the mirror 36. Light reflected off the mirror 36 at this point is directed to the outlet 34 to thereby complete eight passes of light through the cell 31.

In the embodiment of FIGS. 4 and 5, the mirror 36 could have a diameter of 7 cm, with a focal length of 12.7 cm. The entrance aperture 32 could be 6.5 mm and an f number of 2.0. Any suitable means can be employed for supporting the mirror pairs within the chamber. Moreover, the mirrors of the mirror pairs can be formed as single integral structures having two mirror portions obliquely disposed with respect to each other.

The light source can also be selected from any of those commercially available, and may include lasers as well as incoherent sources. Exact dimensions can be determined to suit the individual applications, just as the number of mirror pairs can be chosen to provide the desired number of passes.

If a large number of passes are necessary, some of the oblique mirrors can be positioned at larger radii positions than the radius of the spherical mirror. As a result, the first end of the sampling cell would necessarily become the larger end of the sampling cell. In addition, when many passes are used, or light bundles with large solid angles are employed, field lenses may be placed in one or more of the focus planes between turning oblique mirror pairs. Alternatively, one or more of the mirrors may be curved instead of flat.

Additionally, instead of designing the spherical mirror and oblique mirror pairs such that the points where the light bundle approaches the entrance plane are at the same radius, the sampling cell can be designed such that the points where the light approaches the entrance plane are on two or more arcs of circles at different radii. Alternatively, the sampling cell can be arranged such that the points lie along a straight line or on a rectangular grid.

In the event all the passes at the first end of the sampling cell are at the same radius from the longitudinal axis of the sampling cell, performance can be improved by replacing the large spherical mirror with a special shaped mirror.

It should be noted that in any cross section through the cell axis the large mirror would be an ellipse with its foci in the entrance-exit plane and located at the radius (from the longitudinal axis of the sampling cell) where the center of the entrance and exit are located.

The subject invention has a number of advantages over prior multiple pass sampling cells. For example, when only a few passes are necessary, the diameter of the light bundle can be rather large. This allows the introduction of substantial quantities of light from an extended source, thereby increasing the amount of light passing through the sampling cell. Such an increase in light intensity facilitates the production of higher precision measurements.

Additionally, where a sampling cell is used for accurately measuring gas concentration by applying the Beer-Lambert relation, it is necessary to accurately determine the length of the light path within the sampling cell. The subject invention greatly reduces the possibility of light passing through unintended paths. Consequently, measurements can be made with certainty as to the path traveled by the light bundle.

Every pair of flat mirrors provides a reflective means for generating a multiple pass optical path between the light inlet and light outlet. Each mirror pair further provides means for effecting a lateral transfer of the optical path after every two successive passes through the gas chamber. The lateral transfer ensures that the light exit will not coincide with the light inlet.

While embodiments have been described specifically for one, two and three mirror pairs, additional numbers of mirror pairs could be employed.

The embodiments described herein have been limited to the use of an enclosed cell. The aircraft and nature of the UV mirrors precluded exposing the optical elements to the airstream. However, nothing precludes use of the present invention as an open path device, by removing the walls of the container, and thereby measure in ambient air or in space under conditions where such measurements are useful. Such uses may include fast response measurements of infrared absorption of carbon dioxide and/or water vapor in the air. The measurement is feasible when the wind is allowed to blow across the light beam, which is oriented perpendicular to the wind component. In most cases, this is the vertical wind component (i.e., perpendicular to the ground), which is an intermittent rather than continuous flow. A number of devices have used White cells for this purpose in spite of their obvious disadvantages. Use of a cell is not practical for these measurements because of the length of time required to pump the air through the cell, and because a closed cell that is big enough presents resistance to air motion thereby distorting the wind field and very possibly invalidating the simultaneous air motion measurements needed.

Thus, the present invention relates to open path gas absorption measurements in a compact space using an extended light source (i.e., thermal hot filament, gas discharge, etc.). This could be in the atmosphere or in outer space, or even in a condensed fluid like water.

While it has been shown and described what is presently considered the preferred embodiment of the invention, it will be apparent to those skilled in the art that various changes and modifications may be made therein without departing from the scope of the invention as defined by the appended claims.

What is claimed is:

1. A multiple pass gas absorption cell, comprising:

a gas chamber having first and second opposite axial ends and a longitudinal axis;

a light inlet disposed in the first axial end of the gas chamber, a light outlet disposed in the first axial end and being on a common radius with the light inlet but at a different azimuthal position;

first reflective means, fixedly disposed at the second axial end of the gas chamber, for directing light longitudinally through the gas chamber towards the first axial end; and second reflective means, fixedly disposed at the first axial end of the gas chamber, for directing light reflected off the first reflective means in a direction transverse the longitudinal axis of the gas chamber and longitudinally through the gas chamber towards the second axial end, wherein the light inlet and the light outlet are disposed in a common focal plane of the first reflective means, wherein the first reflective means comprises a spherical mirror having a radius of curvature and a diameter, wherein the light inlet is spaced apart from the spherical mirror by a distance approximating the radius of curvature of the spherical mirror, wherein the light inlet is on a radius approximately one half a radius of the spherical mirror, and wherein a light beam bundle from an extended light source is introduced into the gas chamber through the light inlet;

wherein the diameter of the spherical mirror is only slightly larger than a largest diameter of the light beam bundle.

2. A multiple pass gas absorption cell according to claim 1, wherein the second reflective means comprises a first pair of mirrors disposed in the gas chamber adjacent the first end and in an optical path between the light inlet and light outlet.

3. A multiple pass gas absorption cell according to claim 2, wherein the first pair of mirrors includes first and second mirrors disposed obliquely with respect to each other.

4. A multiple pass gas absorption cell according to claim 2, further comprising a second pair of mirrors disposed in the gas chamber adjacent the first end and in the optical path between the light inlet and light outlet.

5. A multiple pass gas absorption cell according to claim 4, wherein the first pair of mirrors includes first and second mirrors disposed obliquely with respect to each other, and the second pair of mirrors includes third and fourth mirrors disposed obliquely with respect to each other.

6. A multiple pass gas absorption cell according to claim 4, further comprising a third pair of mirrors disposed in the gas chamber adjacent the second end and in the optical path between the light inlet and light outlet.

7. A multiple pass gas absorption cell according to claim 6, wherein the first pair of mirrors includes first and second mirrors disposed obliquely with respect to each other, the second pair of mirrors includes third and fourth mirrors disposed obliquely with respect to each other, and the third pair of mirrors includes fifth and sixth mirrors disposed obliquely with respect to each other.

8. A multiple pass gas absorption cell, comprising:

a gas chamber having first and second opposite axial ends and a longitudinal axis;

a light inlet disposed in the first axial end of the gas chamber;

a light outlet disposed in the first axial end and being on a common radius with the light inlet but at a different azimuthal position;

a spherical mirror fixedly disposed at the second axial end of the gas chamber and having a radius of curvature adapted to direct light longitudinally through the gas chamber towards the first axial end; and a first pair of flat mirrors, obliquely disposed with respect to each other, and fixedly disposed at the first axial end of the gas chamber and being adapted to direct light reflected off the first reflective means in a direction transverse the longitudinal axis of the gas chamber and longitudinally through the gas chamber towards the second axial end, wherein the light inlet and the light outlet are disposed in a common focal plane of the first reflective means, wherein the first reflective means comprises a spherical mirror having a radius of curvature and a diameter, wherein the light inlet is spaced apart from the spherical mirror by a distance approximating the radius of curvature of the spherical mirror, wherein the light inlet is on a radius approximately one half a radius of the spherical mirror, and wherein a light beam bundle from an extended light source is introduced into the gas chamber through the light inlet;

wherein the diameter of the spherical mirror is only slightly larger than a largest diameter of the light beam bundle.

9. A multiple pass gas absorption cell according to claim 8, further comprising a second pair of mirrors disposed in the gas chamber adjacent the first end and in the optical path between the light inlet and light outlet.

10. A multiple pass gas absorption cell according to claim 9, wherein the first pair of mirrors includes first and second mirrors disposed obliquely with respect to each other, and the second pair of mirrors includes third and fourth mirrors disposed obliquely with respect to each other.

11. A multiple pass gas absorption cell according to claim 10, further comprising a third pair of mirrors disposed in the gas chamber adjacent the first end and in the optical path between the light inlet and light outlet.

12. A multiple pass gas absorption cell according to claim 11, wherein the first pair of mirrors includes first and second mirrors disposed obliquely with respect to each other, the second pair of mirrors includes third and fourth mirrors disposed obliquely with respect to each other, and the third pair of mirrors includes fifth and sixth mirrors disposed obliquely with respect to each other.

13. A multiple pass gas absorption cell, comprising:

a gas chamber having first and second opposite axial ends and a longitudinal axis;

a light inlet disposed in the first axial end of the gas chamber;

a light outlet disposed in the first axial end and being on a common radius with the light inlet but at a different azimuthal position; and reflective means for generating a multiple pass optical path between the light inlet and light outlet, the reflective means including means for effecting a lateral transfer of the optical path after every two successive passes through the gas chamber, wherein the light inlet and the light outlet are disposed in a common focal plane of the first reflective means, wherein the first reflective means comprises a spherical mirror having a radius of curvature and a diameter, wherein the light inlet is spaced apart from the spherical mirror by a distance approximating the radius of curvature of the spherical mirror, wherein the light inlet is on a radius approximately one half a radius of the spherical mirror, and wherein a light beam from an extended light source is introduced into the gas chamber through the light inlet;

wherein the diameter of the spherical mirror is only slightly larger than a largest diameter of the light beam bundle.

* * * * *